(12) United States Patent
Drewitz

(10) Patent No.: US 10,792,177 B2
(45) Date of Patent: Oct. 6, 2020

(54) ORTHOSIS FOR CORRECTION OF A VARUS/VALGUS MALALIGNMENT

(75) Inventor: Heiko Drewitz, Gleichen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 308 days.

(21) Appl. No.: 13/695,137

(22) PCT Filed: Mar. 18, 2011

(86) PCT No.: PCT/DE2011/000292
§ 371 (c)(1),
(2), (4) Date: Oct. 29, 2012

(87) PCT Pub. No.: WO2011/134446
PCT Pub. Date: Nov. 3, 2011

(65) Prior Publication Data
US 2013/0053742 A1 Feb. 28, 2013

(30) Foreign Application Priority Data
Apr. 30, 2010 (DE) .......... 10 2010 019 355

(51) Int. Cl.
*A61F 5/00* (2006.01)
*A61F 5/01* (2006.01)

(52) U.S. Cl.
CPC .......... *A61F 5/0113* (2013.01); *A61F 5/0127* (2013.01)

(58) Field of Classification Search
CPC ........ A61F 5/01; A61F 5/0102; A61F 5/0111; A61F 5/0113
(Continued)

(56) References Cited

U.S. PATENT DOCUMENTS 4,554,912 A * 11/1985 Haberman ............... 602/27
4,719,926 A * 1/1988 Nelson ............ A43B 3/0031
36/89
(Continued)

FOREIGN PATENT DOCUMENTS

AT 25437 8/1906
CN 101505691 A 8/2009
(Continued)

OTHER PUBLICATIONS

PCT International Search Report for International Application No. PCT/DE2011/000292, dated Oct. 7, 2011.
(Continued)

*Primary Examiner* — Victoria J Hicks
(74) *Attorney, Agent, or Firm* — Holland & Hart, LLP

(57) ABSTRACT

An orthosis for the correction of a varus/valgus malalignment of a person comprises a support device which in the frontal plane has an L shape and a support limb reaching under the foot of the person and establishing contact with a tread and a splint arrangement extending laterally upwards along the leg, said splint arrangement being connectible to the lower leg of the person via a fastening device. The splint arrangement is subdivided into a contact limb to rest laterally against the foot and a splint to rest laterally against the lower leg and to exert a torque onto the lower leg by a rotary joint which is arranged approximately at the level of the ankle joint. The orthosis allows an effective correction of the malalignment using only one foot part and a splint which extends laterally along the lower leg.

5 Claims, 1 Drawing Sheet

(58) Field of Classification Search
USPC .................. 602/23, 27, 28, 16, 29; 128/882
See application file for complete search history.

(56) References Cited

U.S. PATENT DOCUMENTS

| | | | |
|---|---|---|---|
| 5,797,865 | A | 8/1998 | McDavid |
| 5,830,166 | A * | 11/1998 | Klopf .................... A61F 5/0113 602/16 |
| 7,001,349 | B2 | 2/2006 | Vollbrecht et al. |
| 7,413,555 | B2 | 8/2008 | Wagner et al. |
| 2005/0038364 | A1 | 2/2005 | Vollbrecht et al. |
| 2008/0300525 | A1* | 12/2008 | Shlomovitz ........... A61F 5/0111 602/28 |
| 2010/0106065 | A1 | 4/2010 | Ward |

FOREIGN PATENT DOCUMENTS

| | | |
|---|---|---|
| DE | 3720767 A1 | 6/1986 |
| DE | 4418382 A1 | 11/1995 |
| DE | 10337332 A1 | 3/2005 |
| DE | 10321117 B4 | 9/2006 |
| EP | 1508318 A2 | 2/2005 |
| FR | 359867 A | 4/1906 |
| WO | 03057094 A1 | 7/2003 |

OTHER PUBLICATIONS

Thomas Schmalz et al, The influence of sole wedges on frontal plane knee kinetics, in isolation and in combination with representative rigid and semi-rigid ankle—foot-orthoses, Clinical Biomechanics 21 (Feb. 2006) 631-639, www.elsevier.com/locate/clinbiomech.

Andre-R. Baehler, Orthopaedic Indications, Knee Joint Investigations Techniques, The German Library, pp. 116-118, 1996 Verlag Hans Huber, Bern, English Translation.

Teufel, Orthotics: Peroneus Orthoses, UFO Lower-Limb Managment Orthosis Type 1, pp. 17-19, retrieved Dec. 2016. English Translation.

Teufel, Orthotics: Peroneus Orthotics, Requirements for the Medical Care Product, UFO Lower-Limb Managment Orthosis Type III, pp. 10-16, retrieved Dec. 2016. English Translation.

Leg Orthoses and Bandages 2004, pp. 1-3, Herausgerber: Swissortho, 2004, English Translation.

Rehadat Hilfsmittel, UFO lower-limb management orthosis type I, Valens version, Nov. 2013, pp. 1-2, Cologne Institute for Economic Research, English Translation.

Rehadat Hilfsmittel, Valens Caliper, Nov. 2013, pp. 1-3, Cologne Institute for Economic Research, English Translation.

Rehadat Hilfsmittel, UFO lower-limb management orthosis type III, Nov. 2013, pp. 1-2, Cologne Institute for Economic Research, English Translation.

* cited by examiner

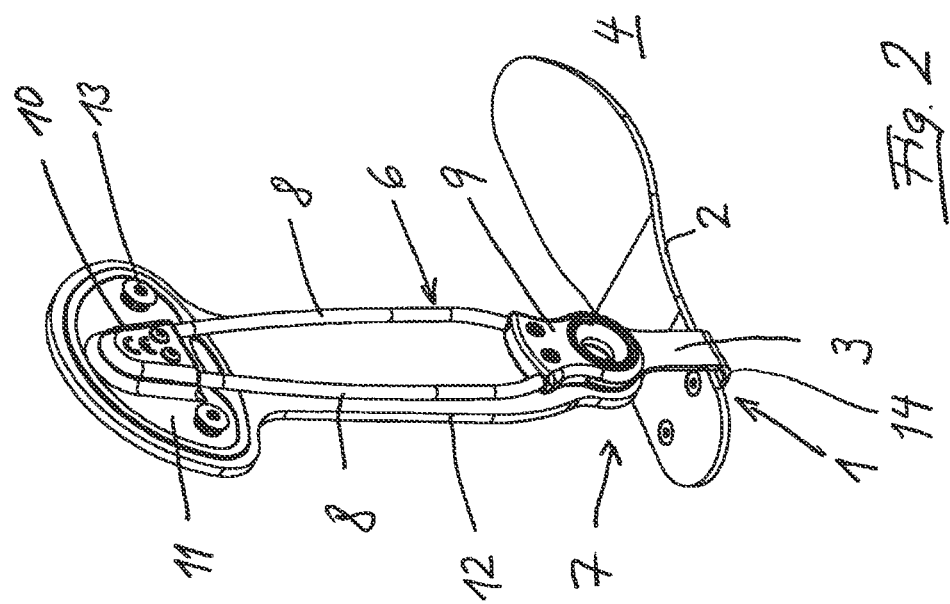
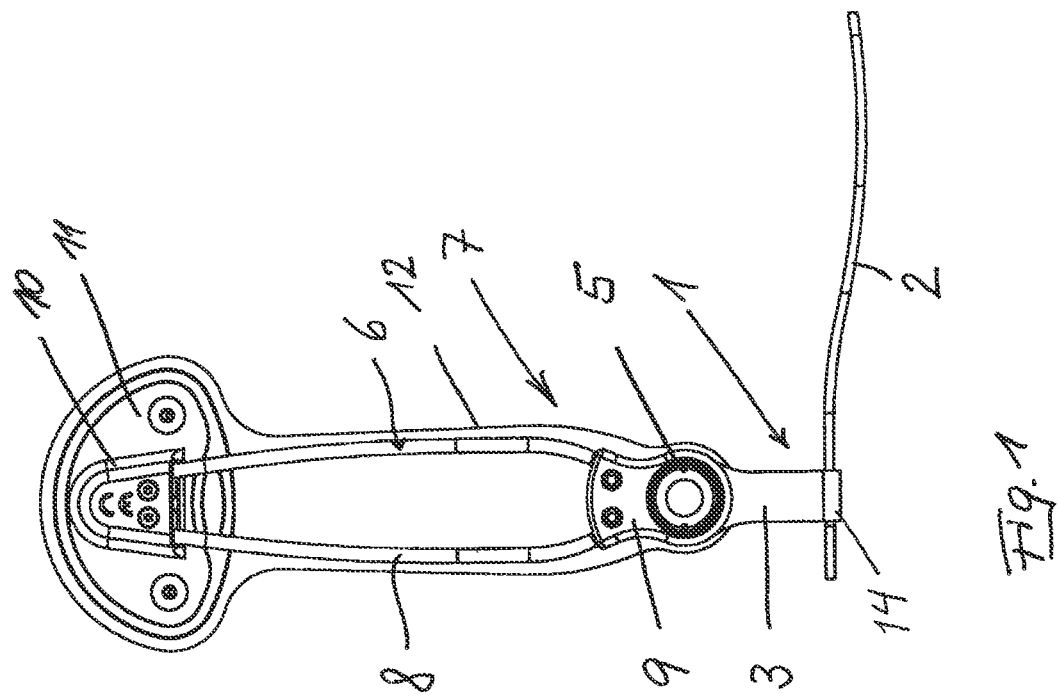

ORTHOSIS FOR CORRECTION OF A VARUS/VALGUS MALALIGNMENT

TECHNICAL FIELD

The invention relates to an orthosis for correcting a leg malalignment of a person, comprising a support apparatus, formed in an L-shaped fashion in the frontal plane with a support limb, which engages below a foot of the person and makes contact with a tread, and with a brace arrangement projecting laterally upward along the leg, which brace arrangement can be connected to the lower leg of the person using an attachment apparatus, wherein a bracket which is rigid under stress is formed at the transition from the support limb to the brace arrangement and the brace arrangement is subdivided by a rotary joint which is arranged approximately level with the ankle joint into a contact limb, provided for lateral contact on the foot, and a brace, provided for lateral contact on the lower leg and for exerting a torque on the lower leg.

BACKGROUND

The leg malalignments considered here are genu valgum or genu varum, which are expressed by a medial or lateral displacement of the frontal central axis of the knee.

In order to correct such a leg malalignment, it is known to use an orthosis which extends along the outer side of the leg with an upper leg part and a lower leg part, the two parts being interconnected by a rotary joint level with the knee joint. In this case, the upper leg part and lower leg part are angled with respect to one another at an angle deviating from 180° such that a torque for correcting the leg malalignment is exerted on the knee joint via the connection between the upper leg part and the upper leg and between the lower leg part and the lower leg. The flexibility of the knee joint is maintained by the rotary joint.

There have also been previous attempts for correcting the correction of leg malalignments by using a torque which acts on the knee joint and is generated with the aid of an orthosis only attached to the foot and lower leg.

In this respect, AT 25437 discloses an orthosis of the type mentioned at the outset, in which the angle between the support limb and the brace arrangement is an acute angle (<90°) or an obtuse angle (>90°), depending on whether a genu varum or genu valgum is corrected. The effectiveness of this orthosis is due to the fact that the support limb is at an angle to the tread and therefore has eccentric support points on the tread. When walking or standing, the load due to the body weight forms a torque which pulls the brace arrangement away from the lower leg or pushes it against the lower leg. Here, the brace and the support limb are connected at a rigid angle with regard to the frontal plane because the rotary joint level with the ankle joint merely allows a rotational movement in the sagittal plane. The pull or pressure acting on the lower leg is in this case dependent on the body weight of the person wearing the orthosis. Moreover, such an orthosis was found not to be effective because the deviation of the support limb when put under pressure on the tread leads to a giving away of the foot relative to the lower leg in the ankle joint, as a result of which the effect sought after by using the orthosis is largely destroyed. The solution described in the aforementioned patent document from the year 1906 was considered ineffectual by experts for the aforementioned reasons.

Accordingly, leg malalignments have been corrected for decades by using the orthoses described at the outset, which are attached to the upper leg by an upper leg brace and attached to the lower leg by a lower leg brace and have a rotary joint level with the knee joint, with the position of the upper leg brace relative to the lower leg brace providing the torque required for correcting the leg malalignment. These orthoses must therefore have a significant size and are therefore complicated. As a result of their size, they have a significant adverse effect on the appearance of the orthosis wearer.

SUMMARY

The invention is therefore based on the object of developing an orthosis for correcting a leg malalignment of a person such that the orthoses can be designed in a less complex and less conspicuous manner.

According to the invention, in order to achieve this object, an orthosis of the type mentioned at the outset is characterized in that the brace is embodied as a resilient element and in that the torque results from a preset pretension of the resilient element relative to the lower leg.

According to the invention, the correction of the leg malalignment is undertaken with the aid of an orthosis which consists of a foot part and a lower leg part, which are interconnected by a rotary joint level with the ankle joint. Here, the support limb and the contact limb are at a fixed angle with respect to one another. With respect to the substantially horizontal support on the tread, the support limb is designed such that there is no or at least no significant change in the angle between the support limb and the tread when a load is applied due to the weight of the person. The torque to be exerted for correcting the leg malalignment results from the pretension of the resilient brace.

The support limb can be formed in an areal fashion and parallel to the tread, for example in the form of a sole. However, on its surface facing the tread, the support limb can also have a slightly convex design in order to obtain slight lateral flexibility in the ankle joint, for example for balancing the body weight.

The orthosis according to the invention therefore does not block the flexibility of the ankle joint by forced bending of the foot with respect to the lower leg. Since the torque for correcting leg malalignment emerges from the resilient arrangement of the brace above the rotary joint, the result is a small orthosis which can be worn in a relatively inconspicuous manner in the region of the foot and lower leg. This maintains the free flexibility of the leg. The flexibility of the knee joint is likewise fully maintained because the orthosis does not project beyond the knee joint. The torque exerted on the lower leg leads to a slight opening of the medial tibial plateau in the wanted direction and therefore enables an effective correction of the leg malalignment over the duration of wearing the orthosis.

BRIEF DESCRIPTION OF THE DRAWINGS

The invention should be explained in more detail below on the basis of an exemplary embodiment illustrated in the drawing. In detail:

FIG. 1 shows a lateral view of an exemplary embodiment of an orthosis according to the invention and FIG. 2 shows a perspective illustration of the orthosis as per FIG. 1.

DETAILED DESCRIPTION

The orthosis illustrated in the drawing is provided for the right leg of an orthosis wearer. It has a foot part 1, which, as seen from the front, has an L-shaped design and is provided with a support limb 2 in the form of a sole part for engaging below the foot of the orthosis wearer. On the lateral side, a contact limb 3 adjoins the support limb 2 at approximately right angles with an angled bracket 14, said contact limb being provided and embodied for lateral contact to the foot of the orthosis wearer. The foot part 1 forms a solid part, the angle of which between support limb 2 and contact limb 3 remains unchanged when subjected to a load. The lower side of the support limb 2 has an areal design relative to a tread 4 such that the angle between the foot part 1 and the tread 4 does not or does not significantly change in the frontal plane when subject to a load during walking or standing. Here, elastic rolling of the tread 4 during walking is possible in the sagittal plane and provided for increasing the comfort when walking. At the upper end of the contact limb 3, the foot part 1 has a connection to a rotary joint 5 by means of which a brace 6 is connected to the foot part 1 such that it can rotate in the sagittal plane. The contact limb 3, the rotary joint 5 and the brace (therefore form a brace arrangement 7 connected to the support limb 2, said brace arrangement extending upward from the support limb 2 and being provided for lateral contact to the foot and lower leg of the orthosis wearer.

In the illustrated exemplary embodiment, the brace is formed by two bent tubes 8, which extend upward from a V-shaped holder 9 at the rotary joint 5 and enter a likewise V-shaped holder 10 situated slightly below the knee of the orthosis wearer.

In a lateral view, the tubes 8 are bent such that they are inserted into the holders 9, 10 at an acute angle to one another and their spacing increases toward the central region. Moreover, the tubes 8 likewise have a bent design in a lateral direction such that, for example, they initially approach the lower leg after leaving the holder 9 in order then to be routed upward to the holder 10 at a smaller angle with respect to the perpendicular.

The rotary joint 5 is approximately level with the ankle joint. Hence the brace 6 illustrated in the drawing is matched to the usual shape of a lower leg, which has a minimal width in the ankle region above the ankle joint before then becoming significantly wider in the calf region. The illustrated orthosis corresponds to this shape, but has a medial tilt of the brace 6 as a result of which a pretension of the resilient brace 6 is generated, with which the brace 6 pushes in the medial direction on the lateral side at the upper end in particular, i.e. just below the knee joint, in order thus to exert a corrective force for a varus gonarthrosis (genu varum).

In the embodiment illustrated in the drawing, the brace 6 formed by the tubes 8 is stabilized by the holders 9, 10, which prevent the tube pieces from bending apart in the direction of the sagittal plane, i.e. in the illustrated width of the brace 6.

The upper holder 10 is attached to a plate 11 pointing at the lower leg, said plate ensuring that the contact pressure is distributed over the lower leg.

The described supporting structure of the orthosis is complemented by cushioning 12 on the inner side of the brace 6, of the rotary joint 5 and of the plate 11 in order to enable comfortable wear of the orthosis on the body parts. An attachment belt, which can be attached to the attachment buttons 13 on the plate 11 and can be embodied as a hook-and-loop closure in order to enable a continuous adjustment to the circumference of the lower leg below the knee of the orthosis wearer, has not been illustrated.

The foot part 1 is attached onto the orthosis wearer by other means, for example by introducing the foot part 1 into a shoe together with the foot of the orthosis wearer.

The illustrated orthosis therefore serves for correcting a varus gonarthrosis (genu varum) by exerting pressure with the brace 6 on the lower leg just below the knee joint. However, the tubes 8 can also be bent such that they form an angle with respect to the contact limb 3 which has a tilt in the lateral direction such that the attachment belt 11 exerts a pulling force on the lower leg below the knee joint in order thus to exert a correcting force for a valgus gonarthrosis (genu valgum). To this end, the bent tubes are rotated by approximately 180° about their respective longitudinal axis in the holders 9, 10.

In principle, it would also be possible to let the orthosis act medially on the lower leg of the orthosis wearer such that a pressure force is exerted for a valgus gonarthrosis and a pulling force is exerted for a varus gonarthrosis. However, there will often be an impediment to walking in such an arrangement, and so, in general, the lateral arrangement is to be preferred.

It is possible to identify from the illustrated exemplary embodiment that the corrective force exerted by the brace 6 only acts on the lower leg of the orthosis wearer above the rotary joint 5. Accordingly, the position of the foot in the foot part 1 or relative to the tread 4 is not influenced by exerting the corrective force, and so the corrective force is not compensated for by a lateral deviation of the foot relative to the lower leg. Rather, the angle between the tread 4 and the foot remains unchanged as a result of the foot part 1, and so the corrective force exerted by the brace 6 is effective where it should be effective in order to relieve the damaged medial (or lateral) region in the medial tibial plateau by means of the corrective force.

The orthosis according to the invention therefore makes it possible for the first time to effectively apply a corrective force in the case of gonarthrosis while having an extent only in the foot region and lower leg region of the orthosis wearer, and so it is possible to dispense with an upper leg part and a knee joint part of the orthosis.

The invention claimed is:

1. An orthosis for correcting a leg malalignment of a person, comprising:
    a support apparatus, formed in an L-shaped fashion in the frontal plane, the support apparatus including a support limb, which is configured to engage below a foot of the person, a contact limb extending vertically from the support limb, and a bracket, which is rigid under stress and is formed at a transition from the support limb to the contact limb;
    a brace configured to be arranged in contact with a side of the lower leg and configured to exert a torque on the lower leg just below the knee to correct knee malalignment, wherein the brace is embodied as a resilient element, the brace is bent at an angle in a lateral direction relative to the contact limb, and the torque results from a preset pretension of the resilient element relative to the lower leg;
    an attachment apparatus configured to connect an upper end of the brace to the lower leg of the person just below the knee;
    a rotary joint connected between the brace and the support apparatus and configured to be arranged approximately level with an ankle joint of the person and in lateral contact on the foot to allow movement of the person's ankle joint;

wherein the preset pretension of the resilient element is configured to exert a corrective force acting only on the lower leg at a location just below the knee.

2. The orthosis as claimed in claim 1, wherein the support limb is formed with a support surface or with central support points in a direction of a tread surface.

3. The orthosis as claimed in claim 1, wherein the brace has tubes which are bent in a shaping manner and which include two free tube ends that enter holders.

4. The orthosis as claimed in claim 1, wherein the brace has a concave curvature above the rotary joint, which concave curvature merges into a convex curvature configured to match a sural shape of the lower leg.

5. The orthosis as claimed in claim 1, wherein the support limb is designed to horizontally support the foot and maintain an angle between the support limb and a ground surface against which the support limb is supported when a load is applied by a weight of the person.

* * * * *